United States Patent [19]

Yasui et al.

[11] Patent Number: 5,473,034
[45] Date of Patent: Dec. 5, 1995

[54] METHOD FOR PRODUCING PROTEIN-SYNTHETIC POLYMER CONJUGATE AND SAID CONJUGATE PRODUCED THEREBY

[75] Inventors: Mitsuo Yasui, Mukoh; Sumita Suguru, Himeji; Uemura Isamu, Kobe, all of Japan

[73] Assignee: Hyogo Prefectural Government, Hyogo, Japan

[21] Appl. No.: 204,389

[22] Filed: Mar. 18, 1994

[51] Int. Cl.$^6$ ............................ C07K 15/12; C07K 3/08
[52] U.S. Cl. .................... 527/200; 527/201; 527/204; 527/207; 530/402
[58] Field of Search ............................ 530/402; 527/200, 527/201, 204, 207

[56] References Cited

U.S. PATENT DOCUMENTS

| | | | |
|---|---|---|---|
| 2,035,348 | 3/1936 | Sly | 527/207 |
| 3,806,417 | 4/1974 | Beaucamp et al. | 527/201 |
| 3,873,478 | 3/1975 | Comte et al. | 527/204 |
| 4,822,867 | 4/1989 | Erhan | 527/207 |

FOREIGN PATENT DOCUMENTS

| | | |
|---|---|---|
| 50-17215 | 2/1975 | Japan . |
| 59-139396 | 8/1984 | Japan . |

*Primary Examiner*—Nathan M. Nutter
*Attorney, Agent, or Firm*—Birch, Stewart, Kolasch & Birch

[57] ABSTRACT

A method for producing an ester of a protein by an esterification reaction of an aqueous solution, fine powder or suspension of a protein having free carboxyl groups with an excess amount of polyfunctional alcohol to esterify the protein; a method for producing a protein-synthetic polymer conjugate from said ester by utilizing a hydroxyl or unsaturated group of a polyfunctional alcohol present in the esterified portion of the protein; and a protein-synthetic polymer conjugate produced thereby.

13 Claims, No Drawings

METHOD FOR PRODUCING PROTEIN-SYNTHETIC POLYMER CONJUGATE AND SAID CONJUGATE PRODUCED THEREBY

TECHNICAL FIELD

The present invention relates to a method for producing a protein-synthetic polymer conjugate and the conjugate produced thereby. More specifically, it relates to a method for producing a protein-synthetic polymer conjugate, wherein a protein-synthetic polymer conjugate is obtained by reacting an alcohol having a functional group with a carboxyl group of amino acids constituting a protein to produce an ester of the protein, or wherein the ester is further reacted with a synthetic polymer material that is reactive with the functional group after esterification.

BACKGROUND ART

Protein, a hydrophilic polymer constituting the living body, has various excellent functions, including biocompatibility and bioactivity such as enzymatic action.

When a protein alone is used as a material, it fails to fully exhibit its excellent functions, because its stability, mechanical strength and workability are low. To compensate for these drawbacks, formation of a conjugate of protein with a synthetic polymer has been intensively studied.

However, it is actually very difficult for a synthetic polymer to form a conjugate with a hydrophilic protein, because the synthetic polymer is usually hydrophobic. As an approach to this problem, it may be possible to utilize a large number of active side chains present in a protein, but protein-based graft polymerization of a monomer requires the use of an aqueous solvent because the reactivity in an organic solvent is poor. Therefore this kind of polymerization has a limit in itself.

With this in mind, the present inventors previously developed a moisture absorbing/releasing material, wherein a small amount of natural polymer is bound to a synthetic polymer by milling gelatin to a fine powder and mechanically kneading the powder in the absence of a solvent. However, its function was subject to limitation because this method is limited to the process for producing a conjugate based on a synthetic polymer.

However, if the content ratio of the protein and synthetic polymer, which are mutually bound, can be freely adjusted and if free shaping is possible, development of various conjugates with never before obtained functions will be possible.

For example, if it is possible to make a highly hydrophilic protein form a conjugate with a synthetic polymer, its affinity to other synthetic polymers becomes high. This not only permits the combined use with other synthetic polymers, but also offers a useful material of good touch or "a moist touch." To achieve this, a design of proteins with high reactivity even in organic solvents is required.

With these circumstances in mind, the present inventors intensively investigated obtaining a protein that is highly reactive in organic solvents.

Although esterification of a compound containing no functional group other than the hydroxyl group, such as a monohydric alcohol, with protein is well known, protein esterification with an alcohol having a functional group other than the hydroxyl group remains yet to be fully clarified.

Directing their attention to the conventional method for esterification of a protein with a monohydric alcohol, the inventors esterified the carboxyl group of protein with a polyfunctional alcohol, and examined the improvement in the reactivity of the protein ester in organic solvents.

As a result, the present inventors found that polyfunctional alcohols, like monohydric alcohols, can be easily esterified with the carboxyl group of a protein, even in the absence of a catalyst, and further that this ester can be used to obtain a protein-synthetic polymer conjugate.

DISCLOSURE OF INVENTION

Specifically, in order to synthesize a protein-synthetic polymer conjugate in the present invention, the first step is to prepare a protein ester having a functional group derived from a polyfunctional alcohol by reacting a polyfunctional alcohol with the carboxyl group of amino acids constituting the protein by esterification.

The second step, which uses an organic solvent such as toluene, dimethylformamide, ethyl acetate, tetrahydrofran, cyclohexane and dimethylsulfoxide, which have seldom been used as a solvent for protein itself because of its low affinity to protein, is to produce a protein-synthetic polymer conjugate by existing polymerization techniques, such as addition polymerization of epoxy resin, raw material compound of urethane resin or other polymerizable vinyl monomers to the protein ester obtained in the first step and graft polymerization of a synthetic polymer to the protein ester.

The present invention is based on the above findings, and relates to:

(1) A method for producing an ester of a protein, characterized by conducting a esterification reaction of an aqueous solution, fine powder or suspension of a protein with an excess amount of a polyfunctional alcohol to esterify a free carboxyl group of the protein;

(2) A method for producing a protein-synthetic polymer conjugate, characterized by using a polyhydric alcohol as a polyfunctional alcohol in method (1), and conducting a urethanation reaction of a compound having an isocyanate group with the hydroxyl group derived from the polyhydric alcohol that is present in the esterified portion of the protein.

(3) A method for producing a protein-synthetic polymer conjugate, characterized by using a polyhydric alcohol as a polyfunctional alcohol in method (1), and allowing the hydroxyl group derived from the polyhydric alcohols present in the esterified portion of the protein to react with a compound having an epoxy group and then undergoing subsequent resinification.

(4) A method for producing a protein-synthetic polymer conjugate, characterized by using an alcohol having an unsaturated bond as a polyfunctional alcohol in method (1); and conducting addition polymerization, in the presence of a polymerization initiator, of a vinyl monomer to the unsaturated group derived from the alcohol having an unsaturated bond present in the esterified portion of the protein, or graft polymerization of a synthetic polymer to the unsaturated group, or graft polymerization of the ester of the protein having the unsaturated group to a synthetic polymer.

(5) The ester of a protein obtained in (1) above, and various protein-synthetic polymer conjugates obtained by the above production methods (2) to (4).

BEST MODE FOR CARRYING OUT THE INVENTION

Each embodiment of the present invention is described below.

(1) The first embodiment (production of ester):

An ester of a protein can be produced by the reaction of an aqueous solution, fine powder or suspension of the protein with an excess amount of a polyfunctional alcohol to thereby esterify a free carboxyl group of the protein.

The protein used in the present invention is not subject to any particular limitation; various polypeptides can be exemplified, including gelatin, collagen, casein, etc. Animal skins such as calf skin, pig skin and sheep skin, such as chrome-tanned leather, containing these polypeptides, may be used as such.

In the present invention, an ester of a protein can be obtained by adding a polyfunctional alcohol to an aqueous solution, fine power or suspension of the protein and conducting an esterification reaction.

The polyfunctional alcohols mentioned here are exemplified by polyhydric alcohols such as diethylene glycol, triethylene glycol, polyethylene glycol, glycerol, butanediol and propanediol, and alcohols having an unsaturated bond such as allyl alcohol, 4-allyl catechol and allyl carbinol. Alcohols having an epoxy group are also acceptable.

Although the amount of the polyfunctional alcohols used is not subject to any particular limitation, it is common to use the polyfunctional alcohol in an excess amount relative to the carboxyl groups in the protein, the appropriate amount being 0.0015 to 0.1 mole per gram of the protein. Esterification can usually be carried out at a reaction temperature in the range from 10° to 100° C. Reaction time is usually in the range from 1 hour to 4 days, though it does not depend on a single factor, since the degree of esterification can be varied according to the amount of polyfunctional alcohol used and reaction temperature.

By the reaction of the polyfunctional alcohol with the protein mentioned above, the carboxyl group of glutamic acid (Glu), aspartic acid (Asp), etc. in the protein can be esterified, to yield a protein with an esterified portion. In such a manner, protein esters having various functional groups of polyfunctional alcohols in the esterified portion of the protein can be obtained. When a polyhydric alcohol is used as the polyfunctional alcohol mentioned above, for example, an ester of a protein having a hydroxyl group in the esterified portion of the protein can be obtained. When an alcohol having an unsaturated bond is used, an ester of a protein having an unsaturated group in the in the esterified portion of the protein can be obtained.

(2) The second embodiment (production of a protein-synthetic polymer conjugate):

In the first embodiment mentioned above, a protein-synthetic polymer conjugate can be produced by using a polyhydric alcohol as a polyfunctional alcohol to synthesize a protein ester having a hydroxyl group derived from a polyhydric alcohol in the esterified portion of the protein, reacting said hydroxyl group with a compound having an isocyanate group to yield a urethane.

The polyhydric alcohols which can be used herein are exemplified by diethylene glycol, triethylene glycol, polyethylene glycol and glycerol, among the above-mentioned polyfunctional alcohols, and alcohols having two or more hydroxyl groups in the molecule thereof such as butanediol and propanediol.

The hydroxyl group present in the esterified portion of the protein of the resulting ester can be urethanated by the reaction of the ester with a compound having an isocyanate group. Specifically, for example, the ester may be reacted with a compound having an isocyanate group and then urethanated with a polyol or a diamine. As a compound having the isocyanate group, a prepolymer of a terminal diisocyanate may be used to urethanate said ester to yield a protein-synthetic polymer conjugate.

The compound having the isocyanate group, the polyol or diamine used herein may be chosen according to the purpose, usually from ordinary ones.

(3) The third embodiment (production of a protein-synthetic polymer conjugate):

In the first embodiment mentioned above, a protein-synthetic polymer conjugate can be produced by using a polyhydric alcohol as a polyfunctional alcohol, forming a protein ester having a hydroxyl group that is derived from the polyhydric alcohol in the esterified portion of the protein, reacting the hydroxyl group with a compound having an epoxy group and then resinifying.

The polyhydric alcohol used herein may be the same as those used in the second embodiment. Compounds having an epoxy group include epichlorohydrin, which may be used to epoxidate the ester, followed by a reaction with, for example, a polyhydric phenol, to cause sequential resin formation, or a resin having an epoxidated end may be reacted with the hydroxyl group of the ester to yield a protein-synthetic polymer conjugate.

(4) The fourth embodiment (production of a protein-synthetic polymer conjugate):

In the above-described first embodiment, a protein-synthetic polymer conjugate can be produced by synthesizing an ester of a protein having an alcohol-derived unsaturated group with an unsaturated bond in the esterified portion of the protein using an alcohol having an unsaturated bond as a polyfunctional alcohol, then carrying out addition polymerization of a vinyl monomer in the presence of a polymerization initiator, or graft polymerization of a synthetic polymer to the unsaturated group, or graft polymerization of the ester of a protein having the unsaturated group to a synthetic polymer.

The alcohols used herein, which have an unsaturated bond, are exemplified by allyl alcohol, 4-allyl catechol and allyl carbinol as mentioned above.

Various methods can be used to produce a protein-synthetic polymer conjugate using an ester having such an unsaturated group, including 1) addition polymerization with various polymerizable vinyl monomers in the presence of a conventional polymerization initiator, 2) graft polymerization of a synthetic polymer to the ester, and 3) graft polymerization of the ester to a synthetic polymer.

The polymerization initiators which can be used in the above-described method 1) are exemplified by benzoyl peroxide and azoisobutyronitrile, and known polymerization techniques based on radiopolymerization, ultraviolet polymerization, polymerization by mechanochemical reaction, etc. may also be used.

Polymerizable vinyl monomers which can be used include vinyl chloride, ethylene, styrene, methyl methacrylate, butadiene and chloroprene. Silicon monomers can also be used.

In the above-described methods 2) or 3), the reaction is carried out by cleaving the unsaturated group of the ester on a synthetic polymer or on a shaped synthetic polymer in the presence of a polymerization initiator to graft the ester to the synthetic polymer, or by grafting a synthetic polymer to the ester. The polymerization initiator used here may be the same as those specified for method 1) above. Synthetic polymers include polyvinyl chloride, polyethylene, polyamide resin, silicon rubber, polybutadiene rubber, polychloroprene rubber and thermoplastic rubber. It should be noted, however, that vulcanized rubbers can be used but are less effective than unvulcanized ones, though they permit grafting.

The protein-synthetic polymer conjugate of the present invention is obtained in the second through fourth embodiments with the ester obtained in the above-described first embodiment as an intermediate. The protein-synthetic polymer conjugate thus obtained is structurally characterized by the presence of a urethane bond in the esterified portion of the protein (obtained in the second embodiment), epoxidation of the esterified portion of the protein (obtained in the third embodiment) and binding of the synthetic polymer to the esterified portion of the protein (obtained in the fourth embodiment).

The present invention is hereinafter described in more detail by means of the following working examples, but is not limited by them.

The presence of an ester bond in the esters obtained in the Examples was confirmed as follows: Qualitative determination: Determined by detection of an ester bond by FT-IR or by a coloring reaction with hydroxamic acid-iron (III).

In the hydroxamic acid-iron (III) coloring reaction, 0.6 ml of an aqueous solution of hydroxylamine (2 mol/1/3.5 N NaOHaq=1/1) is added to 0.2 ml of an about 2 wt % aqueous sample solution, and the mixture is kept standing at 30° C. for 5 minutes. Then, 0.4 ml of 4N HClaq and 0.4 ml of an FeCl$_3$aq solution (10 wt % FeCl$_3$·6H$_2$O/0.1N HClaq) are added.

If an ester is present, the solution develops a red-purple color. Quantitative determination: Determined by the weight method or the NMR method.

In the weight method, the resultant protein is washed with water and dried, after which the weight increment is measured to obtain the percent degree of esterification. In the NMR method, the percent degree of esterification is calculated from the area ratio of the phenylalanine nuclear substitution H in the protein and the =CH$_2$ group H in the allyl alcohol by NMR at 200 MHz.

EXAMPLE 1

4.489 g (dry weight) of an alkali-treated gelatin (produced by Konica Gelatin K.K., α-gelatin of about 100,000 molecular weight) was placed in a glass-stoppered conical flask and dissolved in 10 ml of distilled water. After 5 ml of allyl alcohol was added, the flask was tightly stoppered and a reaction was carried out at 50° C. for 24 hours. To recover the ester, the solvent water and the excessive unreacted allyl alcohol were evaporated in an oven at 50° C. and subsequently completely removed by drying at 80° C. under reduced pressure for 24 hours.

The resulting ester was again dissolved in 10 ml of distilled water and subjected to three cycles of the same procedure as above; the yield of the ester became constant, reaching a final yield of 4.774 g. The resulting fine powder was confirmed to contain an ester bond by absorption at 1724 cm$^{-1}$ in diffusion reflection FT-IR and by color development from yellow to red-purple in the coloring reaction with hydroxamic acid-iron (III). Also, NMR analysis at 200 MHz identified the fine powder as a gelatin ester (gelatin/ allyl alcohol) wherein about 91% of the carboxyl groups of the gelatin were esterified.

EXAMPLE 2

A dry weight of 5.105 g of a chrome-tanned leather (calf skin) powder, milled to not greater than about 10 μm, was placed in a glass-stoppered conical flask together with 5 ml of allyl alcohol to obtain a suspension, followed by a reaction at 50° C. for 24 hours while stirring the suspension using a magnetic stirrer. Next, the excessive allyl alcohol was removed using a rotary evaporator and then completely removed by drying at 40° C. under reduced pressure for 24 hours.

After the ester obtained was washed with 10 ml of distilled water, a small amount of alcohol contained was removed in the same manner as in Example 1. After this procedure was repeated three times, the yield of the ester (chrome-tanned leather/allyl alcohol) reached a constant amount. The final yield obtained was 5.237 g, and the percent degree of esterification based upon weight increment was 37%.

EXAMPLE 3

In a glass-stoppered conical flask, 5 ml of diethylene glycol, 5.256 g of casein (first grade reagent) and 5 ml of 0.1N HCl were placed, followed by a reaction at 50° C. while stirring the mixture using a stirrer. The reaction was stopped 24 hours later, and the reaction product was precipitated in methanol and repeatedly washed with water to completely remove the unbound diethylene glycol. After air drying, the mixture was further dried under reduced pressure to remove the remaining trace amount of water. As a result, 5.358 g of an ester (casein/diethylene glycol) was obtained.

EXAMPLE 4

After 0.793 g of the ester (gelatin/allyl alcohol) obtained in Example 1 and 2 ml of a 2 mmol/l solution of the radical polymerization initiator benzoyl peroxide (hereinafter referred to as BPO) in toluene were placed in a reaction vessel, 0.762 g of a styrene monomer and 5 ml of toluene were further added, followed by nitrogen replacement and 3 hours of reaction at 80° C., and methanol was added to stop the reaction. The resulting graft product was washed with acetone to remove the styrene monomer and the unbound polystyrene contained therein and 0.860 g of a protein-synthetic polymer conjugate (gelatin/polystyrene graft product) was obtained.

EXAMPLE 5

Onto a 2×4 cm plasticizer-free transparent vinyl chloride resin plate, 0.225 g of the ester (gelatin/allyl alcohol) obtained in Example 1 was applied in the form of a powder, and several drops of a 3 mmol/l solution of BPO in dimethyl sulfoxide were added to wet the powder, after which the plate was transferred to a desiccator, followed by a reaction at 80° C. for 3 hours while maintaining a reduced pressure using an aspirator. The reaction product formed a film on the vinyl chloride resin plate. After the plate was boiled in water for 1 hour, about 80% insoluble protein remained on the vinyl chloride resin plate as a protein-synthetic polymer conjugate (gelatin/vinyl resin plate graft product) bound to the plate.

As a control experiment, gelatin which had not been chemically modified was applied onto a resin plate as a BPO-free dimethyl sulfoxide solution in the same manner as above. To the resulting product, water was added, which was then boiled for 15 minutes. As a result, all the gelatin on the vinyl chloride resin plate dissolved.

EXAMPLE 6

An 86% ester of gelatin (gelatin/butanediol) was obtained in the same manner as in Example 3 except that diethylene glycol was replaced with butanediol and casein was replaced with gelatin. This ester was dried at 80° C. under reduced pressure for 24 hours to remove water therefrom, after which 0.102 g of the ester was dissolved in dimethyl sulfoxide to yield an about 15% solution. While stirring this solution, tolylene diisocyanate was added at an —NCO/OH equivalence ratio of 1.02. After vigorous stirring, the mixture was casted on a glass plate. About 30 minutes later, the glass plate was immersed in water to remove the solvent. As a result, obtained was a transparent flexible tough film-like protein-synthetic polymer conjugate (protein/urethane compound conjugate) which did not dissolve even after 3 hours of boiling in water.

EXAMPLE 7

5 g of an ester (gelatin/butanediol) obtained in the same manner as in Example 6 and 0.2 g of caustic soda were dissolved in 25 ml of distilled water. Separately, 2 ml of epichlorohydrin was placed in a three-mouthed flask equipped with a dripping funnel containing 5 ml of dimethyl sulfoxide and a condenser. Next, a solution of the ester in caustic soda was added drop by drop using the dripping funnel over a period of about 10 minutes, followed by a reaction for 5 hours while stirring the mixture. After completion of the reaction, the mixture was poured into an excessive amount of acetone, filtered and washed, after which it was dried in a vacuum to yield an epoxidated intermediate of the ester. Subsequently, 4 g of this epoxidated intermediate was dissolved in 25 ml of dimethyl sulfoxide. This solution was placed in a three-mouthed flask equipped with a condenser and a dripping funnel, and heated to 50° C., and 8.5 mmol of bisphenol A was added. After the bisphenol A was dissolved, an equivalent molar amount of a 40% caustic soda solution was gradually added, followed by a reaction for 6 hours. After the reaction was stopped, the reaction product was filtered with an excessive amount of acetone and repeatedly washed.

Next, to remove the caustic soda from the reaction product, the reaction product was placed in a Visking tube and dialyzed in a sodium borate solution of pH 7.2 for 2 days, after which it was dried, to yield about 5.3 g of a product. To modify this 5.3 g to a setting resin, the same procedure as for the above-described epoxidated intermediate was repeated, and obtained was a protein-synthetic polymer conjugate (protein/epoxy compound conjugate) whose terminal hydroxyl group was epoxidated.

The epoxidated protein thus obtained could be crosslinked with an ordinary setting agent for epoxy resin setting.

EXAMPLE 8

4.683 g of the ester (casein/diethylene glycol) of Example 3, previously dried at 60° C. under reduced pressure for 24 hours to remove water therefrom and 10 ml of dimethyl sulfoxide were placed in a reaction vessel. Next, while stirring this solution using a stirrer, 0.952 g of butanediol and 10 ml of a dimethyl sulfoxide solution were added, and subsequently a solution of 0.363 g of diphenylmethane diisocyanate in 5 ml of dimethylformamide was added. Next, the reaction vessel was heated to 50° C., followed by a reaction for about 2 hours, after which the reaction product was precipitated in methanol, the polymer was recovered, and the unchanged mixture remaining in the polymer was removed by 24 hours of Soxhlet extraction with ethyl acetate.

The protein-synthetic polymer conjugate (protein/urethane compound conjugate) thus obtained was a powder, whose surface condition was analyzed by FT-IR based on the diffusion method. An absorption assigned to an urethane bond was noted at 1740 cm$^{-1}$, and other absorptions each assigned to an ester bond, at 1320 cm$^{-1}$ and 1230 cm$^{-1}$.

EXAMPLE 9

5 ml of a 3 mmol/l solution of BPO in toluene was placed in a polymerization tube, and 5.25 g of the ester (gelatin/allyl alcohol) (fine powder state) of Example 1, previously dried at 60° C. under reduced pressure for 24 hours to remove water therefrom, was added. 1.0 ml of a chloroprene monomer purified by a conventional method was further dissolved in this toluene mixture, the air in the polymerization tube was replaced with nitrogen, the tube was sealed, and polymerization was initiated at 60° C.

After 6 hours of polymerization, the tube was opened, the reaction mixture was poured into methanol, and the polymer was recovered.

The resulting polymer was subjected to 24 hours of Soxhlet extraction with benzene to remove the residual monomer and homopolymer.

Drying under reduced pressure yielded about 5.5 g of a polymer. This polymer was identified to be in a state (a protein-synthetic polymer conjugate) wherein the rubber was bound to the protein surface by detection of a chloroprene double bond at 1640 cm$^{-1}$ in the differential spectrum obtained by the diffusion method (FT-IR analysis).

INDUSTRIAL APPLICABILITY

According to the present invention, it is possible not only to modify synthetic polymers or proteins by covering the synthetic polymer surface with a protein or by covering the protein surface with a synthetic polymer but also to produce protein-synthetic polymer conjugates of various compositions.

The present invention is therefore applicable to new functional products, such as functional separation membranes, biocompatible materials, biodegradable polymers, protein-based water-resistant adhesives and protein-based flame resistant materials.

The present invention is expected to be widely used in various fields from food industry producing protein materials to plastic, rubber and fine chemical industries.

We claim:

1. A method for producing an ester of a protein, comprising conducting an esterification reaction of an aqueous solution, fine powder or suspension of a protein having free carboxyl groups with an excess amount of a polyfunctional alcohol selected from the group consisting of diethylene glycol, triethylene glycol, polyethylene glycol, glycerol, butanediol, propanediol, allyl alcohol, 4-allyl catechol, allyl carbinol and epichlorohydrin, to thereby esterify a free carboxyl group of the protein, wherein the esterification reaction is carried out at a temperature of 10° to 100° C. for a period of time effective to complete the esterification reaction.

2. A method for producing a protein-synthetic polymer conjugate, comprising the steps of conducting an esterification reaction of an aqueous solution, fine powder or suspension of a protein having free carboxyl groups with an excess amount of a polyhydric alcohol selected from the group consisting of diethylene glycol, triethylene glycol, polyethylene glycol, glycerol, butanediol and propanediol, to thereby esterify a free carboxyl group of the protein and introduce a hydroxyl group derived from the polyhydric alcohol into the esterified portion of the protein, and conducting a urethanation reaction of a compound having an isocyanate group with the hydroxyl group derived from the polyhydric alcohol present in the esterified portion of the protein.

3. A method for producing a protein-synthetic polymer conjugate, comprising the steps of conducting an esterification reaction of an aqueous solution, fine powder or suspension of a protein having free carboxyl groups with an excess amount of a polyhydric alcohol selected from the group consisting of diethylene glycol, triethylene glycol, polyethylene glycol, glycerol, butanediol and propanediol, to thereby esterify a free carboxyl group of the protein and introduce a hydroxyl group derived from the polyhydric alcohol into the esterified portion of the protein, and allowing the hydroxyl group derived from the polyhydric alcohol present in the esterified portion of the protein to react with epichlorohydrin and then to undergo subsequent resinification.

4. A method for producing a protein-synthetic polymer conjugate, comprising the steps of conducting an esterification reaction of an aqueous solution, fine powder or suspension of a protein having free carboxyl group with an excess amount of an alcohol having an unsaturated bond selected from the group consisting of allyl alcohol, 4-allyl catechol and allyl carbinol, to thereby esterify a free carboxyl group of the protein and introduce an unsaturated group derived from the alcohol having an unsaturated bond into the esterified portion of the protein, and conducting addition polymerization, in the presence of a polymerization initiator, of a polymerizable vinyl monomer to the unsaturated group derived from the alcohol having an unsaturated bond present in the esterified portion of the protein, graft polymerization of a synthetic polymer selected from the group consisting of polyvinyl chloride, polyethylene, polyamide resin, silicon rubber, polybutadiene rubber, polychloroprene rubber and thermoplastic rubber to the unsaturated group derived from the alcohol having an unsaturated bond, or graft polymerization of the esterified protein having said unsaturated group to a synthetic polymer selected from the group consisting of polyvinyl chloride, polyethylene, polyamide resin, silicon rubber, polybutadiene rubber, polychloroprene rubber and thermoplastic rubber.

5. The method according to claim 1, 2, 3, or 4, wherein the protein is gelatin, collagen or casein.

6. The method according to claim 1, 2, 3, or 4, wherein skin selected from the group consisting of calf skin, pig skin, and sheep skin is used as a protein source.

7. The method according to claim 1, 2, 3, or 4, wherein the amount of polyfunctional alcohol, polyhydric alcohol, or alcohol having an unsaturate bond used in the esterification reaction is 0.0015 to 0.1 mole per gram of protein.

8. The method according to claim 1, wherein the polymerization initiator is benzoyl peroxide or azoisobutyronitrile.

9. The method according to claim 1, wherein the polymerizable vinyl monomer is selected from the group consisting of vinyl chloride, ethylene, styrene, methyl methacrylate, butadiene and chloroprene.

10. An ester of a protein obtained by the method according to claim 1.

11. A protein-synthetic polymer conjugate obtained by the method according to claim 2, wherein the esterified portion of the protein has a urethane bond.

12. A protein-synthetic polymer conjugate obtained by the method according to claim 3, wherein the esterified portion of the protein is epoxidated.

13. A protein-synthetic polymer conjugate obtained by the method according to claim 1, wherein the synthetic polymer is bound to the esterified portion of the protein.

* * * * *

UNITED STATES PATENT AND TRADEMARK OFFICE
CERTIFICATE OF CORRECTION

PATENT NO. : 5,473,034

DATED : December 5, 1995

INVENTOR(S) : Mitsuo Yasui et al

It is certified that error appears in the above-identified patent and that said Letters Patent is hereby corrected as shown below:

On the title page, item [75],
IN THE INVENTORS:

Change: "Sumita Suguru" to --Suguru Sumita-- and

"Uemura Isamu" to --Isamu Uemura--

Signed and Sealed this

Fifth Day of March, 1996

*Attest:*

BRUCE LEHMAN

*Attesting Officer*   *Commissioner of Patents and Trademarks*